(12) United States Patent
Grassano et al.

(10) Patent No.: US 6,197,336 B1
(45) Date of Patent: Mar. 6, 2001

(54) FAST DISSOLVING COMPOSITIONS HAVING ANALGESIC ACTIVITY

(75) Inventors: Alessandro Grassano; Maurizio Marchiorri; Mauro Di Toro; Franco Castegini, all of Milan (IT)

(73) Assignee: Zambon Group S.p.A., Milan (IT)

( * ) Notice: Subject to any disclaimer, the term of this patent is extended or adjusted under 35 U.S.C. 154(b) by 0 days.

(21) Appl. No.: 09/320,831

(22) Filed: May 26, 1999

(30) Foreign Application Priority Data

Jul. 30, 1998 (IT) .............................. MI98A1774

(51) Int. Cl.$^7$ ....................................... A61K 9/14
(52) U.S. Cl. ..................... 424/464; 424/465; 424/466; 424/474; 424/479; 424/486; 574/557
(58) Field of Search ..................... 424/464–466, 424/474, 479, 480–482, 483, 484–486; 514/557

(56) References Cited

U.S. PATENT DOCUMENTS

| | | |
|---|---|---|
| 4,548,990 | 10/1985 | Mueller et al. . |
| 4,681,897 | 7/1987 | Brand . |
| 4,689,218 | 8/1987 | Gazzaniga et al. . |
| 4,834,966 | 5/1989 | Gazzaniga et al. . |
| 4,837,031 | 6/1989 | Denton . |
| 4,851,444 | 7/1989 | Sunshine et al. . |
| 4,873,231 | 10/1989 | Smith . |
| 4,911,921 | 3/1990 | Denton et al. . |
| 5,019,563 | 5/1991 | Hunter et al. . |
| 5,034,416 | 7/1991 | Smith . |
| 5,104,648 | 4/1992 | Denton et al. . |
| 5,200,558 | 4/1993 | Kwan . |
| 5,238,831 | 8/1993 | Mutsaers et al. . |
| 5,240,712 | 8/1993 | Smith et al. . |
| 5,262,171 | 11/1993 | Login et al. . |
| 5,262,179 | 11/1993 | Gregory et al. . |
| 5,288,507 | 2/1994 | Sims et al. . |
| 5,360,925 | 11/1994 | Chabrier de Lassauniere et al. . |
| 5,380,927 | 1/1995 | Paradies et al. . |
| 5,431,916 | 7/1995 | White . |
| 5,445,827 | 8/1995 | Fritsch et al. . |
| 5,458,879 | 10/1995 | Singh et al. . |
| 5,480,652 | 1/1996 | Bru-Magntez et al. . |
| 5,480,999 | 1/1996 | Chabrier de Lassauniere et al. . |
| 5,500,226 | 3/1996 | Stroppolo et al. . |
| 5,510,385 | 4/1996 | Stroppolo et al. . |
| 5,519,057 | 5/1996 | Loew et al. . |
| 5,560,913 | 10/1996 | Kupper . |
| 5,560,926 | 10/1996 | Franz et al. . |
| 5,567,437 | 10/1996 | Bru-Magniez et al. . |
| 5,597,583 | 1/1997 | Grattan . |
| 5,631,296 | 5/1997 | Birrenbach et al. . |
| 5,645,857 | 7/1997 | Stroppolo et al. . |
| 5,780,046 | 7/1998 | Humber et al. . |
| 5,840,769 | 11/1998 | Kolter et al. . |
| 5,853,762 | 12/1998 | Myers et al. . |
| 5,869,101 | 2/1999 | Moeller et al. . |

FOREIGN PATENT DOCUMENTS

| | | |
|---|---|---|
| 36 38 414 | 5/1987 | (DE) . |
| 44 10 470 | 9/1994 | (DE) . |
| 0 369 228 | 5/1990 | (EP) . |
| 2 602 141 | 5/1988 | (FR) . |
| 2 279 250 | 1/1995 | (GB) . |
| WO 93/09763 | 5/1993 | (WO) . |
| WO 97/30699 | 8/1997 | (WO) . |
| Wo 00/06125 | 2/2000 | (WO) . |

OTHER PUBLICATIONS

H.F. Mark, et al., Encyclopedia of Polymer Science and Engineering, vol. 17, pp. 224–225, "N–Vinyl Amide Polymers", 1989.

D.R. Karsa, et al., The Royal Society of Chemistry., "Excipients and Delivery Systems for Pharmaceutical Formulations", pp. 80–81, 1995.

Primary Examiner—Neil S. Levy
(74) Attorney, Agent, or Firm—Oblon, Spivak, McClelland, Maier & Neustadt, P.C.

(57) ABSTRACT

An analgesic composition useful in the preparation of fast dissolving tablets is provided, where the composition is the result of combining ibuprofen, arginine, linear PVP and an alkaline bicarbonate to which usual excipients for the preparation of tablets are added.

15 Claims, No Drawings

FAST DISSOLVING COMPOSITIONS HAVING ANALGESIC ACTIVITY

BACKGROUND OF THE INVENTION

1. Field of the Invention

The present invention relates to an analgesic composition useful for preparing fast dissolving tablets containing ibuprofen and arginine and the tablets made therefrom.

2. Discussion of the Background

Ibuprofen is the International common name of the compound 2-(4-isobutylphenyl)-propionic acid, which is a known drug with analgesic, as well as anti-inflammatory and antipyretic, activity of broad diffusion.

In U.S. Pat. No. 4,279,926, ibuprofen salts with basic amino acids such as arginine and lysine have been described.

In U.S. Pat. No. 4,689,218 effervescent compositions of ibuprofen containing arginine together with 20–30% by weight of bicarbonate and 25–40% by weight of sodium bitartrate have been described.

The described formulations are useful for preparing drinkable aqueous solutions.

In U.S. Pat. No. 4,834,966 non-effervescent compositions are disclosed consisting, as a base, of a ternary mixture consisting of ibuprofen, 1.1 to 1.5 mol% arginine per mole of ibuprofen and sodium bicarbonate in a weight amount between 0.25 and 0.75 times the weight of ibuprofen.

These formulations are disclosed as very suitable for the preparation of granulates quickly soluble in water.

The administration of the so obtained aqueous solutions assures a fast analgesic effect which is achieved in about ten minutes.

Sachets containing the granulate of U.S. Pat. No. 4,834,966 are on the market. In some countries, and in particular in the U.S.A., preparations in the form of a sachet are not particularly appreciated by the public, who generally prefer the use of tablets in the treatment of conditions which need an analgesic drug.

The commercially available tablets containing ibuprofen do not have a particularly fast effect because they require about 30 minutes to completely dissolve and reach the blood stream.

In order to obtain a quick dissolution of the active principle, the present inventors tried preparing tablets starting from the ibuprofen-arginine-sodium bicarbonate ternary mixture of the above mentioned U.S. Pat. No. 4,834,966.

Unfortunately, it was impossible to obtain satisfactory results because the resulting tablets were too friable and subject to fragmentation during manufacturing and packaging.

SUMMARY OF THE INVENTION

Accordingly, one object of the present invention is to provide analgesic tablets having good workability and fast dissolution so as to assure a prompt analgesic effect.

This and other objects of the invention have been satisfied by the discovery of a composition comprising ibuprofen, arginine, linear polyvinylpyrrolidone (PVP) and a reduced amount of an alkaline bicarbonate, and a tablet prepared therefrom.

DETAILED DESCRIPTION OF THE PREFERRED EMBODIMENTS

The present invention relates to an analgesic composition comprising: ibuprofen; from 1.1 to 1.5 moles of arginine per mole of ibuprofen; from 0.5 to 10% of linear PVP with respect to the weight of ibuprofen; and from 5 to 10wt% of a bicarbonate with respect to the weight of ibuprofen.

The present invention further relates to the use of the above composition to provide tablets that are fast dissolving and fast acting. The tableting composition also includes normal excipients useful for the preparation of tablets.

Preferably ibuprofen is contained in amounts of from 100 to 400 mg/tablet, more preferably in an amounts of 100, 200 mg/tablet, most preferably in an amount of 200 mg/tablet.

Arginine is contained in the present composition in an amount of from 1.1 to 1.5 moles per mole of ibuprofen, preferably from 1.1 to 1.3 moles per mole of ibuprofen and more preferably in an amount of 1.2 mole per mole of ibuprofen.

Linear PVP is preferably a PVP having an average K value, determined according to the method described in the U.S. Pharmacopoeia XXIII, of from 25 to 90, more preferably from 50 to 90, most preferably PVP K90. It is used in an amount of from 0.5 to 10 wt.% based on weight of ibuprofen, preferably in an amount of from 2 to 8 wt.% with respect to the weight of ibuprofen.

The bicarbonate can be any bicarbonate salt that is pharmaceutically acceptable, preferably sodium or potassium bicarbonate. The bicarbonate is present in an amount of from 5 to 10 wt.%, preferably from 7 to 10 wt.% with respect to the weight of ibuprofen.

Within the context of the present description the identity of the components and amounts thereof refer to the weight and identity of the starting materials used in preparing the composition. It is possible that during preparation of the composition and/or tablets, some interaction or reaction may occur between two or more components. To the extent that such interaction or reaction occurs the present invention is intended to cover such occurrences.

Normal excipients useful in the preparation of the tablets include, but are not limited to: lubricants such as magnesium stearate, sodium stearyl fumarate and sodium benzoate; anti-adherents such as talc and polyethylenglycol; glidants such as colloidal silica; diluents such as dicalcium phosphate, cellulose (for example microcrystalline cellulose) and its derivatives, carbohydrates and polyalcohols such as saccharose, xylitol and lactose; disintegrants such as crosslinked vinylic polymers (such as crosslinked PVP), derivatives of starch and of cellulose such as sodium carboxymethyl-starch and sodium croscarmelose; wetting agents such as TWEEN 80 (Trademark registered by ICI of Americas for polysorbate) and sodium lauryl sulphate.

Suitable excipients and their amounts can be readily determined by those of ordinary skill in the art according to the methods normally used in pharmaceutical technology. However, in the present invention, it is important to avoid excipients that would cause a significant decrease in tablet dissolution rate. Further, excipients must allow a good workability of the tablet.

In preparing the tablet of the present invention it is preferable to prepare a granulate with the mixture of ibuprofen, arginine and linear PVP, to mix it with the bicarbonate and the excipients, and then to compress.

When desired, the tablets can be film coated with a coating readily soluble in the gastric environment.

Suitable coatings can be prepared using conventional tablet coating compositions and methods. Preferred coatings include OPADRY II (sold by Colorcon; a mixture of hydroxypropyl methyl cellulose, pigments and a plasticizer), EUDRAGIT (sold by Rohm Pharma; a methacrylic acid ester polymer) and a combination of OPADRY II with saccharose.

The granulate can be prepared by direct granulation of the three components (ibuprofen, arginine and linear PVP) in the desired amounts or, after a first granulation of arginine with melted ibuprofen, by granulating a second time with linear PVP.

Both granulates obtained according to the above described methods are then screened, dried, combined with bicarbonate and any selected excipient(s) in the desired amounts and compressed in suitable molds for obtaining the desired tablets which can then be film coated, if desired.

In addition to good handling and workability, the tablets of the present invention provide complete dissolution of the active ingredient in about 10 minutes or less. Consequently the release is faster with respect to the commercially available ibuprofen based analgesic tablets (see example 5 below).

Generally, linear PVP is considered a binder at the amounts used in the present invention, and would be thus expected to inhibit dissolution or have little or no effect on dissolution. While Login et al, U.S. Pat. No. 5,262,171, discloses the use of non-crosslinked PVP in tablets to provide improved drug dissolution rate, the best dissolution seen is in acetaminophen tablets containing 1–2% of PVP by weight is 30–40% dissolution within 60 minutes. This is not an improvement when one considers the dissolution of ibuprofen tablets which normally only takes about 30 minutes. The present inventors have found that use of PVP in the amounts of the present invention in an ibuprofen tablet provides suprisingly improved dissolution of ibuprofen tablets to provide complete dissolution of the active ingredient in about 10 minutes or less.

EXAMPLES

Having generally described this invention, a further understanding can be obtained by reference to certain specific examples which are provided herein for purposes of illustration only and are not intended to be limiting unless otherwise specified.

Example 1

Method for the Preparation of a Granulate of Ibuprofen, Arginine and Linear PVP Into an Erweka planetary mixer equipped with a thermostatic jacket bowl the entire quantity of ibuprofen was charged and melted at a temperature of 80°C. under continuous stirring.

After all ibuprofen was entered, arginine, PVP and boiling water were added in that order. After about 10 minutes of continuous stirring, a creamy mass was obtained which was slowly cooled down to room temperature thus obtaining a solid granular mass.

Drying was completed by placing the granulate in a whirlpool static oven regulated at a temperature of 45°C. for about 15 hours.

An alternative procedure involved preparing the ibuprofen and arginine granulate, to which powdered linear PVP was added and a second granulation of the mixture at with cold water was carried out. The wet granulate obtained was dried in a whirlpool static oven. The alkaline bicarbonate and the excipients were then added.

Example 2

Alternative Method for the Preparation of Ibuprofen, Arginine and Linear PVP Granulate Into a fast granulator, water and arginine were sequentially introduced. When the arginine was partially dissolved, ibuprofen and linear PVP were added in sequence, and the mixture warmed under continuous stirring for about 30 minutes to obtain a creamy mass.

The creamy mass was then dried under vacuum for about 50 minutes. At the end of drying the obtained mass was screened through an oscillating granulator equipped with a 1.5 mm sieve.

To the obtained granulate, bicarbonate and the excipients were then added.

The above described granulation method was also used in the preparation of an ibuprofen-arginine granulate to which powdered linear PVP was subsequently added.

The resulting mixture was granulated with cold water and the wet granulated product was dried in a static oven or directly into the granulator. The bicarbonate and excipients were then added.

Example 3

Preparation of Tablets

The granulate containing ibuprofen-arginine and linear PVP, obtained according to the procedure described in the example 1 or in the example 2, and to which bicarbonate and excipients were added, was compressed to the desired weight.

Example 4

By operating according to the procedure described in example 3, the tablets whose composition is reported in the Table 1 were prepared.

TABLE 1

|  | Tablets (mg) | | | | | | |
| --- | --- | --- | --- | --- | --- | --- | --- |
| Ingredients | A | B | C | D | E | F | G |
| Ibuprofen | 200 | 200 | 200 | 200 | 200 | 400 | 400 |
| Arginine | 185 | 185 | 185 | 185 | 185 | 370 | 370 |
| PVP K90 | 5.4 | 5.4 | 5.4 | 5.4 | 5.4 | 10.8 | 10.8 |
| Sodium bicarbonate | 20 | 20 | 20 | 15 | 20 | 40 | 40 |
| Microcrystalline cellulose | 156 |  |  | 156 | 141 | 103 |  |
| Lactose |  | 156 |  |  |  |  | 103 |
| Dicalcium phosphate |  |  | 156 |  |  |  |  |
| Sodium croscarmelose |  |  |  | 30 |  |  |  |
| Sodium carboxymethyl starch |  |  | 30 |  |  |  | 50 |
| Crosslinked PVP | 30 | 30 |  |  | 30 | 50 |  |
| Magnesium stearate | 3.0 | 3.0 | 3.0 | 3.0 | 3.0 | 5.0 | 5.0 |
| Colloidal silica | 0.6 | 0.6 | 0.6 | 0.6 | 0.6 | 1.2 | 1.2 |
| Tablet total weight (mg) | 600 | 600 | 600 | 600 | 600 | 980 | 980 |

Example 5

Determination of the Dissolution Rate of Tablets of the Present Invention

Determination of the dissolution rate was carried out by applying the method described in the U.S. Pharmacopeia XXIII, NF XVII, supplement No. 5, the content of which is hereby incorporated by reference.

Into a dissolution bath a solution of pH 7.2 phosphate buffer was charged and the liquid was thermostated at a temperature of 37°C.

The tablet to be checked was then charged. Under continuous stirring by paddle at 50 rpm, the amount of ibuprofen in solution, expressed in percentage released as a function of time, was measured.

The tablets of the invention has an excellent dissolution rate in comparison with commercially available tablets containing the same amount of ibuprofen.

As an example, the ibuprofen contained in tablet A (see Table 1) was completely in solution in 10 minutes according to the above described test, while a tablet of MOTRIN® (Upjohn) and one of ANTALGIL® (Jannsen-Cilag), containing the same amount of ibuprofen of tablet A, showed the release of a percentage of ibuprofen in solution of about 45% and 65% respectively, after 10 minutes.

It was necessary to wait at least 30 minutes before observing complete dissolution of the ibuprofen contained in the MOTRIN® and ANTALGIN® tablets.

The present application is based on Italian Patent Application MI98A001 774, filed with the Italian Patent Office on Jul. 30, 1998, the entire contents of which are hereby incorporated by reference.

Obviously, additional modifications and variations of the present invention are possible in light of the above teachings. It is therefore to be understood that within the scope of the appended claims, the invention may be practiced otherwise than as specifically described herein.

What is claimed is:

1. An analgesic composition, comprising a composition resulting from combining (a) Ibuprofen, (b) from 1.1 to 1.5 moles of Arginine per mole of Ibuprofen, (c) from 0.5 to 10 wt.% of linear PVP based on weight of Ibuprofen, and (d) from 5 to 10 wt.% of a bicarbonate based on weight of Ibuprofen.

2. A tablet prepared from a composition resulting from combining (a) Ibuprofen, (b) from 1.1 to 1.5 moles of Arginine per mole of Ibuprofen, (c) from 0.5 to 10 wt.% of linear PVP based on weight of Ibuprofen, and (d) from 5 to 10 wt.% of a bicarbonate based on weight of Ibuprofen, and optionally, one or more conventional excipients used in tabletting.

3. The tablet according to claim 2, wherein the ibuprofen is present in an amount of from 100 to 400 mg.

4. The tablet according to claim 2, wherein the ibuprofen is present in an amount of from 200 to 400 mg.

5. The tablet according to claim 2, wherein the arginine is present in an amount of from 1.1 to 1.3 moles per mole of Ibuprofen.

6. The tablet according to claim 5, wherein the Arginine: Ibuprofen molar ratio is 1.2:1.

7. The tablet according to claim 2, wherein the linear PVP has an average K value of from 25 to 90.

8. The tablet according to claim 7, wherein the linear PVP is PVP K90.

9. The tablet according to claim 2, wherein the bicarbonate is sodium or potassium bicarbonate.

10. The tablet according to claim 2, wherein Ibuprofen is present in an amount of from 200 to 400 mg, Arginine is present in an amount of 1.2 moles per mole of Ibuprofen, the linear PVP is PVP K90 and the bicarbonate is sodium bicarbonate.

11. The tablet according to claim 2, wherein said tablet further comprises a film coating.

12. The tablet according to claim 11, wherein said film coating is a coating selected from the group consisting of (i) mixtures of hydroxypropyl methyl celluose, pigments and plasticizer, (ii) methacrylic acid ester polymers and (iii) combinations of (i) with saccharose.

13. A tablet prepared from a composition resulting from combining:

200 mg Ibuprofen 185 mg Arginine 5.4 mg PVP K90

20 mg sodium bicarbonate 156 mg microcrystalline cellulose 30 mg crosslinked PVP 3 mg magnesium stearate; and 0.6 mg colloidal silica.

14. The tablet according to claim 13, wherein said tablet further comprises a film coating.

15. The tablet according to claim 14, wherein said film coating is a coating selected from the group consisting of (i) mixtures of hydroxypropyl methyl celluose, pigments and plasticizer, (ii) methacrylic acid ester polymers and (iii) combinations of (i) with saccharose.

* * * * *